United States Patent [19]

Gautsch

[11] Patent Number: 5,514,255

[45] Date of Patent: May 7, 1996

[54] VERTICALLY STACKED TRAYS OVERFLOWING LIQUID CONGEALING INTO ELECTROPHORESIS GEL, AND OPTIONAL COMBINATION SPACER-COMBS BETWEEN THE TRAYS

[76] Inventor: James Gautsch, c/o BIO 101, Inc., 1060 Joshua Way, Vista, Calif. 92083

[21] Appl. No.: 377,866

[22] Filed: Jan. 25, 1995

[51] Int. Cl.⁶ .................................................... G01N 27/26
[52] U.S. Cl. .......................... 264/104; 204/466; 204/620; 425/117
[58] Field of Search ............................ 204/180.1, 299 R; 62/340; 249/53 R, 126, 127, 129, 130, 141

[56] References Cited

U.S. PATENT DOCUMENTS

| | | | |
|---|---|---|---|
| 4,366,941 | 1/1983 | Harris | 249/120 |
| 4,795,541 | 1/1989 | Hurd et al. | 204/299 R |
| 4,909,977 | 3/1990 | Hurd et al. | 264/261 |
| 5,012,655 | 5/1991 | Chatterton | 62/340 |
| 5,200,045 | 4/1993 | Warren et al. | 204/180.1 |
| 5,275,710 | 1/1994 | Gombocz et al. | 204/299 R |

*Primary Examiner*—T. Tung
*Assistant Examiner*—Alex Noguerola
*Attorney, Agent, or Firm*—William C. Fuess

[57] ABSTRACT

Multiple, typically 5+, trays of an identical special configuration are vertically stacked one atop the next, end-to-end reversed. Each tray has an overflow feature, normally in the form of either (i) a portion of a side that is reduced in height so as to form a lip, (ii) a corner hole protected by a removable baffle of selectable height, or (iii) a threaded standpipe that may be screwed to variable height. The overflow feature permits that liquid will overflow each tray only upon reaching a predetermined height in a reservoir of the tray. A liquid poured in the top tray cascades downwards from tray to tray, filling each tray to a uniform even level and ultimately reaching the bottom tray of the stack. The liquid that is within each tray is permitted to gel, forming thereby a gel state material that is suitable to receive samples upon which electrophoresis may be conducted. Combination spacer and toothed comb elements are optionally inserted between the stacked trays. These spacer-comb elements serve to (i) space apart the stacked trays so that any untoward and undesired wicking of liquid onto the underside of the tray is especially precluded, and to simultaneously (ii) place arrayed small slits, or wells, in the gel—into which wells samples, upon which electrophoresis is ultimately conducted, are inserted.

7 Claims, 4 Drawing Sheets

FIG. 12
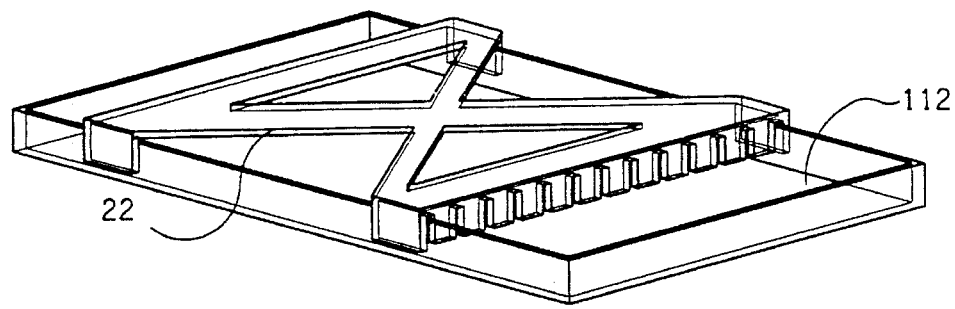
FIG. 13
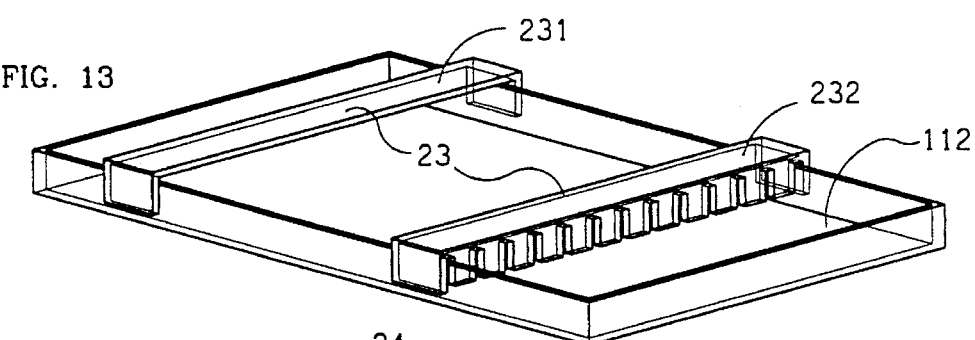
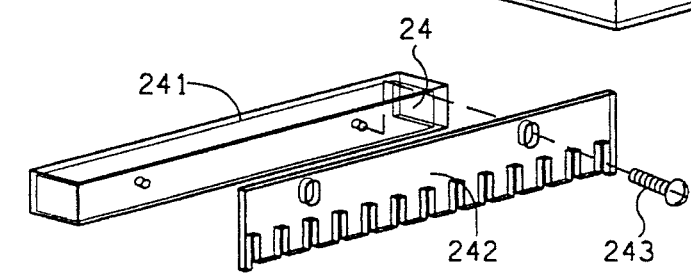
FIG. 14
FIG. 15a
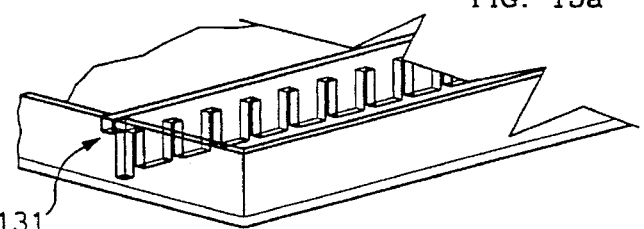
FIG. 15b
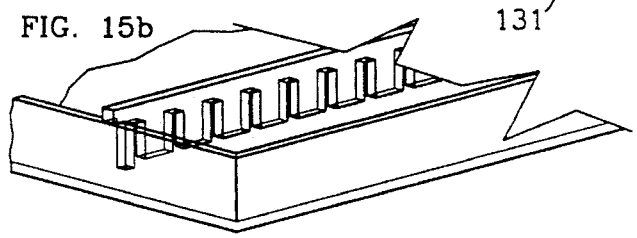
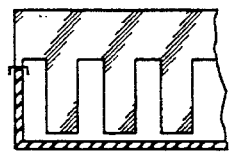
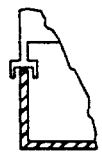
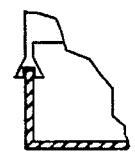
FIG. 16a    FIG. 16b    FIG. 16c    FIG. 16d    FIG. 16e

VERTICALLY STACKED TRAYS OVERFLOWING LIQUID CONGEALING INTO ELECTROPHORESIS GEL, AND OPTIONAL COMBINATION SPACER-COMBS BETWEEN THE TRAYS

BACKGROUND OF THE INVENTION

1. Field of the Invention

The present invention generally concerns the preparation of gels, typically agarose gels, that are suitable to receive samples upon which electrophoresis is performed.

The present invention particularly concerns an apparatus and a method for the easy simultaneous preparation of multiple trays of gels, typically agarose gels, that are suitable to receive samples upon which electrophoresis is performed.

2. Description of the Prior Art

Agarose gel electrophoresis is commonly used for both analytical and preparative separation of DNA fragments. Standard agarose gels separate DNA fragments from ≈0.1 to 25 kilobases, or kb, whereas pulsed-field agarose gels resolve molecules from ≈10 to >2000 kb. Descriptions of standard and pulsed-field agarose gel electrophoresis, as well as parameters affecting resolution of large DNA fragments, are presented in standard textbooks. At least three different protocols employing agarose gels to prepare DNA fragments are known. An agarose gel has the properties of an electric circuit.

One leading protocol for using agarose gel electrophoresis as a simple and highly effective method for the separation, identification and purification of ≈0. to 25 kb DNA fragments can be divided into three stages. First, a gel is prepared with an agarose concentration appropriate for the size of DNA fragments to be separated. Second, the DNA samples are loaded into the sample wells and the gel is run at a voltage and for a time period that will achieve optimal separation. Third and finally, the gel is stained or, if ethidium bromide has been incorporated into the gel and into the electrophoresis buffer, visualized directly upon illumination with ultraviolet (UV) light.

In order to conduct agarose gel electrophoresis, an agarose gel must be prepared. This preparation is the subject of the present invention.

Preparation typically commences by sealing the edges of a clean, dry, glass plate (or the open ends of the plastic tray supplied with the electrophoresis apparatus) with autoclave tape so as to form a mold. An electrophoresis buffer (usually 1×TAE or 0.5×TBE) sufficient in amount so as to fill the electrophoresis tank and to prepare a gel is prepared. An amount of powdered agarose is added to a measured quantity of electrophoresis buffer in an Erlenmeyer flask or a glass bottle with a loose-fitting cap. The same batch of electrophoresis buffer is used in both the electrophoresis tank and the gel.

The neck of the Erlenmeyer flask is loosely plugged. The slurry of powdered agarose and buffer is heated in a boiling-water bath or a microwave oven sufficiently so as to permit all of the grains of agarose to dissolve. The dissolved solution is cooled to 60° C., and if desired, ethidium bromide is added.

The liquid is poured into the mold and permitted to cool to produce a gel. The higher the concentration of agarose, the quicker the gel hardens.

In order to produce slits, or wells, in the gel—into which wells samples undergoing electrophoresis will be inserted—a separate comb is typically positioned 0.5–1.0 mm above the glass plate, or base of the mold. The teeth of the comb form a series of linearly aligned wells when the liquid agarose solution is added to the mold. When the comb is properly manually positioned above the plate, or base of the mold, then it is typically supported on its outer teeth so that its inner teeth will be automatically lifted slightly above, and clear of, the plate.

After the gel is completely set both the comb and autoclave tape are carefully removed, and the gel is mounted in the electrophoresis tank. Just enough electrophoresis buffer is added so as to cover the gel to a depth of about 1 mm.

A sample of DNA is mixed with a desired gel-loading buffer. This mixture is slowly loaded into the slits, or wells, of the submerged gel using a disposable micropipette, an automatic micropipettor or a pasteur pipette. Electrophoresis is then performed.

This prior art procedure for the production of a tray of gel, typically an agarose gel, is (i) labor intensive, and thus (ii) expensive, (iii) tedious, and (iv) ill-adapted to efficiencies of scale because a large number of gel trays are roughly more difficult to make than is a single gel tray in proportion to the numbers thereof.

Moreover, the slits, or wells, that are formed in the gel may be of improper or inconsistent depth in accordance that the manual alignment procedure induces errors.

Admittedly, separation by process of electrophoresis of such samples as are later inserted within the slits, or wells, of the gel may accord a certain registration upon viewing (or photographing) that is based on the innate visual properties of the samples. However, it is illogical, and of dubious soundness as a scientific procedure, that successive gels upon which electrophoresis is performed should not be, insofar as is possible, identical. Although exact chemical identity may not be possible between successive gels that are not simultaneously prepared (the present invention will be seen to greatly abet simultaneous preparation of multiple gels), any significant mechanical variation in gel size and thickness, and the locations and depths of the slits (wells) locations in the gels should be, insofar as is possible, strictly avoided.

Presently, the greatest problem occurs with adjusting the depths of the slits should a one, predetermined, slit depth offered by current equipments prove unsatisfactory. Precision machined combs that are matched to gel trays, and which are accurately positionable thereon by action of tongues and grooves, are known. Variable numbers of slits, or wells, may be selected (in accordance that the comb has a greater, or smaller, number of teeth). However, these slits, or wells, are necessarily of differing depths in gels of various thicknesses. Sometimes it is sufficient, and desired, that all slits, or wells, in all of a number of gels should be formed to be at a uniform height, nominally 1 mm, above the base of the tray at their lowermost extension. The present precision gel combs accord this capability. However, it is sometimes desirable to leave a greater thickness below the wells. The present system does not support of creating wells having a variably selectable depth, which depth may, nonetheless to being variably selectable, be uniform from gel tray to gel tray across as large number of gel trays.

Accordingly, it would be desirable if the limitations of the present procedures for the production of agarose gels could be overcome, and if a large number of gel trays complete with precision located and arrayed slits, or wells, could be reliably, easily and inexpensively made. Moreover, it would be desirable if the numbers and three-dimensional positions—especially the extent above gel tray bottom—of the slits, or wells, which are formed in the gel could be, nonetheless to being variably selectable, precisely controllable. "Precisely controllable" means that two or more gel trays might each be made at separate times to custom mechanical characteristics that are effectively identical. For example, it would be useful if, as an arbitrary example, a gel tray having the physical dimensions of 20 cm by 30 cm bed dimension containing a gel of a (relatively thick) 7 mm perforated at exactly 10 slits of 1.0 mm each at positioned 1 cm from a short side wall, each slit to a (relatively high) 1.5 mm above the base of the tray could be repetitively reliably made, and re-made. This precision over a range of dimensions—especially as relate to the extent of the slits above the base of the gel tray—is effectively impossible with present apparatus, and procedures.

The present invention will be seen to concern an apparatus and method for greatly (i) reducing the labor, and thus (ii) reducing the expense, (iii) reducing the tedium, and (iv) enhancing the efficiency of producing large numbers of gel trays by introducing economies of scale to the entire process.

SUMMARY OF THE INVENTION

In one of its aspects, the present invention contemplates a system and method for preparing multiple trays of a gel state material, normally an agarose gel, all in one step at the same time. In another, separate and severable, one of its aspects, the present invention contemplates an apparatus for conveniently forming an array of wells, each of which is suitable to receive a sample upon which electrophoresis may be performed, in a gel state material held within a tray. In still further aspects, the present invention contemplates a system and method for efficiently producing multiple trays of each containing a gel state material, normally an agarose gel, that is replete with arrayed wells which wells of are suitable to receive samples that undergo electrophoresis.

In a first aspect of the present invention, multiple trays of an identical special configuration are vertically stacked, one atop the next. Each tray has and defines a shallow reservoir and an overflow port from the reservoir. The successive stacked trays are in a same top-bottom orientation, but are typically and preferably reversed end-to-end one tray to the next.

A liquid, normally a hot agarose solution, is then poured into the reservoir of the top tray. The liquid fills this top tray's reservoir to a predetermined depth, and then overflows this top tray through the overflow port, flowing downward into a next lower tray in the stack. The liquid continues to overflow each tray in turn, cascading downwards from tray to tray as each tray is filled to a uniform even level and ultimately reaching the bottom tray of the stack. The liquid that is within each tray is permitted to gel, thereby forming a gel state material that is suitable to receive samples upon which electrophoresis may be conducted.

The process may optionally be abetted by the insertion of combination spacer and toothed comb, or spacer-comb, elements between the stacked trays. In its spacer function each element to (i) space apart the stacked trays so that any untoward and undesired wicking of liquid onto the underside of an overflowing tray is more effectively precluded. In its simultaneous comb function, each element has and presents teeth that extend downwards into the reservoir of an underlying tray, thereby to (ii) prevent the liquid from occupying an array of small volumes in the reservoir of the tray. By this action, when the liquid gels then an array of small slits, or wells, will have been formed in the gel state material. Samples upon which electrophoresis is performed may be later be inserted into these arrayed wells.

In particular detail of construction, each tray is substantially in the shape of a nearly flat typically rectangular parallepiped body having and presenting a shallow trough, or reservoir. A tray is typically, and preferably, made from ultraviolet (UV) transparent acrylic plastic. Each tray is suitably sized and configured so as to be vertically stacked with a number of other trays in a vertical stack, and may be so aided by the optional inclusion of interlocking detentes, normally at the tray corners. The trays need not be, and are not normally, stacked in the same orientation in the stack, but are instead reversed 180° in direction along their long axis from one tray to the next.

Each tray has (i) a substantially flat interior reservoir, (ii) an overflow outlet from which liquid received into the reservoir will flow out of the reservoir when a predetermined liquid level is reached in the reservoir, and (iii) a top opening to the reservoir located so that it may be disposed in position below the overflow outlet of any immediately overlying tray in the vertical stack of trays. The trays are commonly rectangular.

The overflow outlet may be in the form of any of (i) a lip, less than the normal height of the sides of the reservoir, that is normally slightly indented from a side of the rectangular tray, (ii) a baffle of predetermined height, less than the walls of the reservoir, that protects a hole that is normally located in a one corner of the reservoir, (iii) a standpipe, typically spaced apart slightly from the sides of the reservoir normally near a corner, that is of lessor height than the walls of the reservoir, or (iv) any mechanical construction that simply permits the reservoir of the tray to fill to a predetermined level and then directs the overflowing fluid downwards from the tray in a preset course.

The top opening of the tray's reservoir may be coextensive with the entire reservoir of the tray itself, or may be more constrained in accordance that the tray's reservoir may be partially covered by an optional cover, and/or an optional spacer-comb, which elements may have, in some of their configurations, the effect of covering a portion of the tray's reservoir. Regardless of its extent, a top opening to the reservoir is positioned so as to fall in position directly below the egress of overflowing fluid from a superior tray in the vertical stack. The trays so configured permit liquid poured in the topmost tray of a stack to cascade downwards from tray to tray, filling each tray to a predetermined depth, in a similar manner of a classic water clock.

In another of its aspects, the present invention contemplates an apparatus usable so as to prepare from a liquid, normally an agarose gel solution, a flat sheet of a gel state material having and defining an array of wells, wherein each well is suitable to receive a sample upon which electrophoresis may be performed.

The apparatus includes (i) a tray having a base and sides defining a substantially flat and shallow interior reservoir; and (ii) a "comb" member at least partially overlying the reservoir of the tray. To the extent the comb member so overlies the reservoir of the tray it forms a partial cover thereto. The comb member has linearly arrayed teeth in the manner of a comb. The comb member typically and preferably interacts with mechanical features of the order of guides, or detentes, on the tray in order that it and its teeth may be easily precisely located relative to the tray and the tray's reservoir.

The teeth of the comb member extend, when the comb member is in position overlying the tray and its reservoir, downward into the reservoir. An array of small volumes—corresponding to the volumes occupied by the teeth—is therein established within the reservoir by the teeth of the comb member. No liquid poured or otherwise entered into the tray's reservoir can enter into these volumes because they are occupied by the teeth of the member.

Accordingly, when a liquid material is poured into the tray while the comb member is in its typically precise location at least partially overlying the tray's reservoir, and after the liquid material is permitted to gel, then a separation of the comb member from the tray leaves an array of precisely located voids in the gel state material located within the tray's reservoir. These arrayed voids, or slits, or wells, are of suitable size, depth and placement so as to receive samples upon which electrophoresis is performed.

Both aspects of the invention may beneficially be combined, permitting the quick and efficient preparation of a number of trays, each of which trays contains a gel state material replete with arrayed wells, all at the same time.

These and other aspects and attributes of the present invention will become increasingly clear upon reference to the following drawings and accompanying specification.

BRIEF DESCRIPTION OF THE DRAWINGS

FIG. 12 is a diagrammatic perspective view of a second preferred embodiment of the optional combination spacer-combs, located between the trays, previously seen in another embodiment in FIG. 7.

FIG. 13 is a diagrammatic perspective view of a third preferred embodiment of the optional combination spacer-combs, located between the trays, previously seen in other embodiments in FIGS. 7 and 12.

FIG. 14 is a diagrammatic perspective view of a fourth preferred embodiment of the optional combination spacer-combs, located between the trays, previously seen in other embodiments in FIGS. 7, 12 and 13

FIG. 15, consisting of FIG. 15a and FIG. 15b, is a partial, detail, diagrammatic perspective view of the interaction of any of the embodiments of spacer-combs previously seen in FIGS. 7 and 12–14 with an optional detente feature that may be incorporated into any of the embodiments of vertically stacked trays in accordance with the present invention.

FIG. 16, consisting of FIGS. 16a through 16e, is a diagrammatic perspective view of an adjustable fifth preferred embodiment of the optional combination spacer-combs, located between the trays, previously seen in other embodiments in FIGS. 7 and 12–14.

DESCRIPTION OF THE PREFERRED EMBODIMENT

The prior art procedure of the preparation of an agarose gel used to conduct agarose gel electrophoresis is diagrammed in FIGS. 1 through 6.

Figure 1:
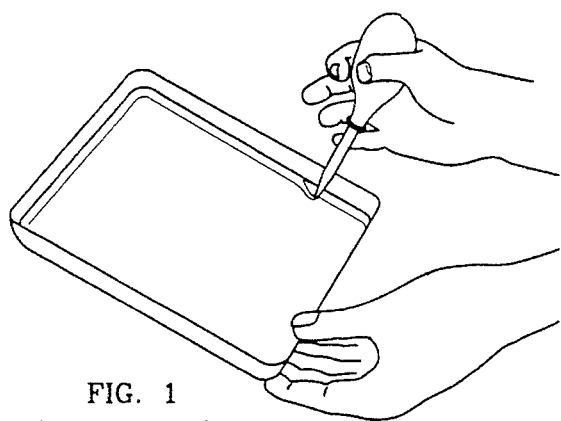
FIGS. 1 through 6 are diagrammatic perspective views of steps in the prior art process of preparing an Agarose gel.

The preparation typically commences by sealing the edges of a clean, dry, glass plate (or the open ends of the plastic tray supplied with the electrophoresis apparatus) with autoclave tape so as to form a mold as is shown in FIG. 1. Sufficient electrophoresis buffer (usually 1×TAE or 0.5× TBE) is prepared so as to both fill the electrophoresis tank and prepare the gel. The correct amount of powdered agarose (as may readily be determined by tables in textbooks, and/or by manufacturer's instructions) is added to a measured quantity of electrophoresis buffer in an Erlenmeyer flask or a glass bottle with a loose-fitting cap. The buffer should not, and does not, occupy more than 50% of the volume of the flask or bottle.

The same batch of electrophoresis buffer must be used in both the electrophoresis tank and the gel. Small differences in ionic strength or pH create fronts in the gel that can greatly affect the mobility of DNA fragments.

The neck of the Erlenmeyer flask is next loosely plugged with laboratory paper tissue. When a glass bottle is used the cap must be loose. The slurry is heated in a boiling-water bath or a microwave oven for at least the minimum time required to permit all of the grains of agarose to dissolve. Wearing an oven mitt, the preparer gingerly swirls the bottle or flask from time to time to make sure that any grains sticking to the walls enter the solution. The agarose solution must not be allowed to become superheated or it may boil violently. Undissolved agarose appears as small "lenses" floating in the solution. The volume of the solution should not be permitted to decreased by evaporation during boiling, and the solution should be replenished with water if necessary.

The dissolved solution is cooled to 60° C., and if desired, ethidium bromide (from a stock solution of 10 mg/ml in water) to is added a final concentration of 0.5 ug/m. (Ethidium bromide is a powerful mutagen and is moderately toxic. Gloves are to be worn when working with solutions that contain this dye. After use, these solutions should be decontaminated. Stock solutions of ethidium bromide should be stored in light-tight containers (e.g., in a bottle completely wrapped in aluminum foil) at room temperature.)

During preparation of gels containing high concentrations of agarose (2% or above), the solution is permitted to cool quickly to 70° C., and is poured to produce a gel immediately. The higher the concentration of agarose, the quicker the gel hardens. Problems caused by premature hardening of the gel can be avoided by using sieving grades of low-gelling-temperature agarose. However, these grades of agarose are suitable only for analytical electrophoresis, since DNA fragments eluted from the gel are frequently contaminated with inhibitors that prevent further enzymatic manipulation.

Figure 2:
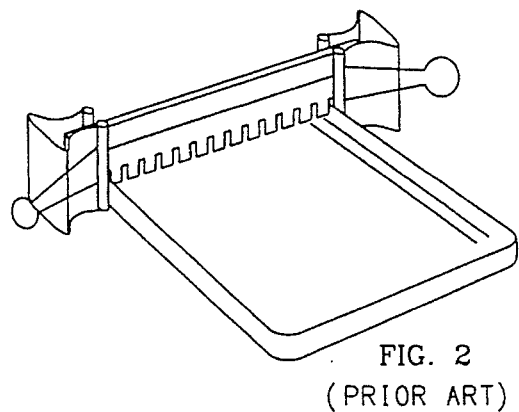

Using a pasteur pipette, the edges of the mold are sealed with a small quantity of the agarose solution, as is further shown in FIG. 1. The seal is then permitted to set. A separate comb is positioned 0.5–1.0 mm above the plate so that a complete well is formed when the agarose is added, as is shown in FIG. 2. If the comb is closer to the glass plate, there is a risk that the base of the well may tear when the comb is withdrawn, allowing the sample to leak between the gel and the glass plate.

Some combs are designed with their two outer teeth slightly longer than the internal teeth. When the comb is positioned above the plate, it is supported on the outer teeth; the inner teeth are automatically lifted clear of the glass plate. (See FIG. 11 for illustration of a commensurate principle in the comb of the present invention). The disadvantage of this design is that the wells made by the outer teeth cannot be used during the subsequent electrophoresis.

Figure 3:
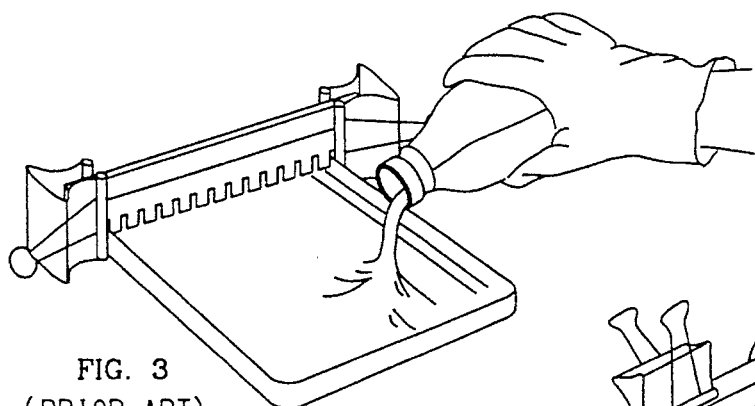

The remainder of the warm agarose solution is next poured into the mold, as is shown in FIG. 3. The gel is preferably made to be between 3 mm and 5 mm thick. No air bubbles should be permitted to form under or between the teeth of the comb.

When gels that contain low concentrations of agarose (<0.5%) are prepared, a supporting gel (1% agarose) is first poured without wells. This gel is permitted to harden at room temperature on the glass plate or plastic tray. The lower-percentage gel is then poured directly on top of the supporting gel. This reduces the chances that the lower-percentage gel will fracture during subsequent manipulations (photography, processing for Southern hybridization, etc.) Both gels should be made from the same batch of buffer, and ethidium bromide must be added to both gels or to neither.

Figure 4:
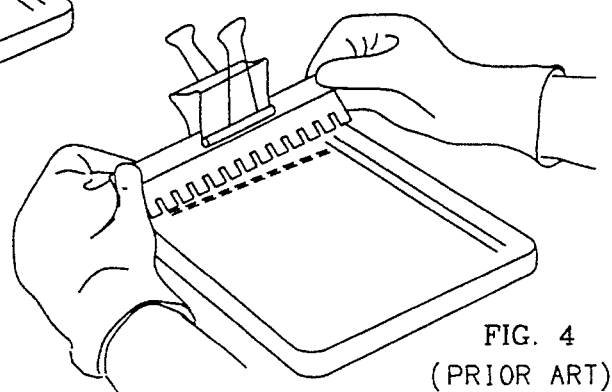
Figure 5:
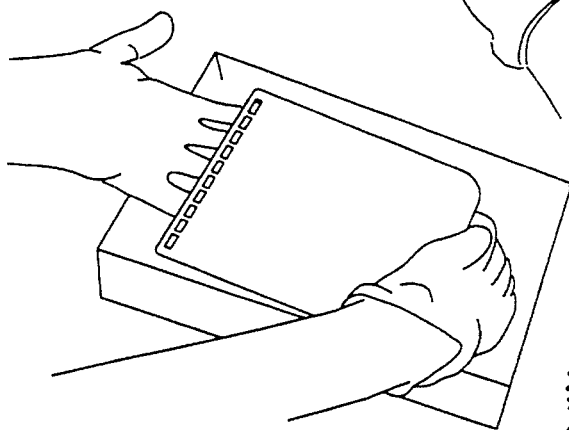

After the gel is completely set (30–45 minutes at room temperature), the comb and autoclave tape are carefully removed as shown in FIG. 4, and the gel is mounted in the electrophoresis tank as shown in FIG. 5.

Gels cast with low-melting-temperature agarose and gels that contain less than 0.5% agarose should be chilled to 4° C. and run in a cold room.

Just enough electrophoresis buffer must be added so as to cover the gel to a depth of about 1 mm.

A sample of DNA is mixed with a desired gel-loading buffer. This mixture is slowly loaded into the slots of the submerged gel using a disposable micropipette, an automatic micropipettor, or, with a very steady hand, a pasteur pipette.

Gel-loading buffers are usually made up from six-fold concentrated solutions. Tenfold concentrated solutions can also be prepared if needed.

The maximum amount of DNA that can be applied to a slot depends on the number of fragments in the sample and their sizes. The minimum amount of DNA that can be detected by photography of ethidium-bromide-stained gels is about 2 ng.

Figure 6:
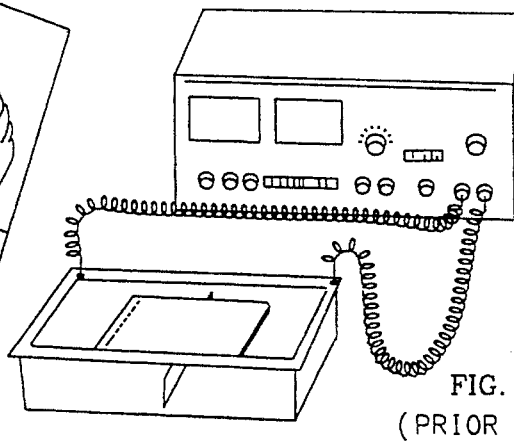

The final performance of prior art electrophoresis is illustrated in FIG. 6.

Precision-machined polycarbonate combs adjustable to the desired height above the gel tray (or above cooling platform with use of a Gel Comb Bridge) are commercially available. Combs available for the 14 cm wide units typically come with 1, 3 (one large well with two marker lanes on each side), 5, 10, 12, 16 or 20 wells in widths of 1.0 mm, 2.0 mm or 3.0 mm. Combs available for 20 cm wide units typically come with 1, 3 (one large well with two marker lanes on each side), 5, 8, 12, 16, 20, 30 or 40 wells with thicknesses of 1.0 mm, 2.0 mm or 3.0 mm.

Gel trays are often fabricated from U-V transparent acrylic to enable direct reading of ethidium bromide stains. Grooves in the gel tray for placement of combs allow single run or two simultaneous short runs. Trays are typically made from ¼"-thick acrylic plastic to prevent heat distortion of tray during application of hot agarose.

Gel Comb Bridges can be ordered for either 14 or 20 cm-wide units. A bridge accessory holds the gel comb in position when it is desired to pour directly onto the gel bed without the use of a gel tray.

As previously explained in the Background of the Invention section of this specification, the overall prior art procedure for the production of tray of gels, typically agarose gels, that are suitable to receive samples upon which electrophoresis is conducted suffers from being (i) labor intensive, and thus (ii) expensive, (iii) tedious, and (iv) ill-adapted to efficiencies of scale, a large number of gel trays being roughly more difficult to make than a single gel tray in proportion to the number thereof.

In accordance with the present invention a new apparatus and method greatly (i) reduces the labor, and thus (ii) the cost, (iii) reduces the tedium, and (iv) enhances the efficiency of producing large numbers of gel trays by introducing economies of scale to the entire process.

Figure 7:
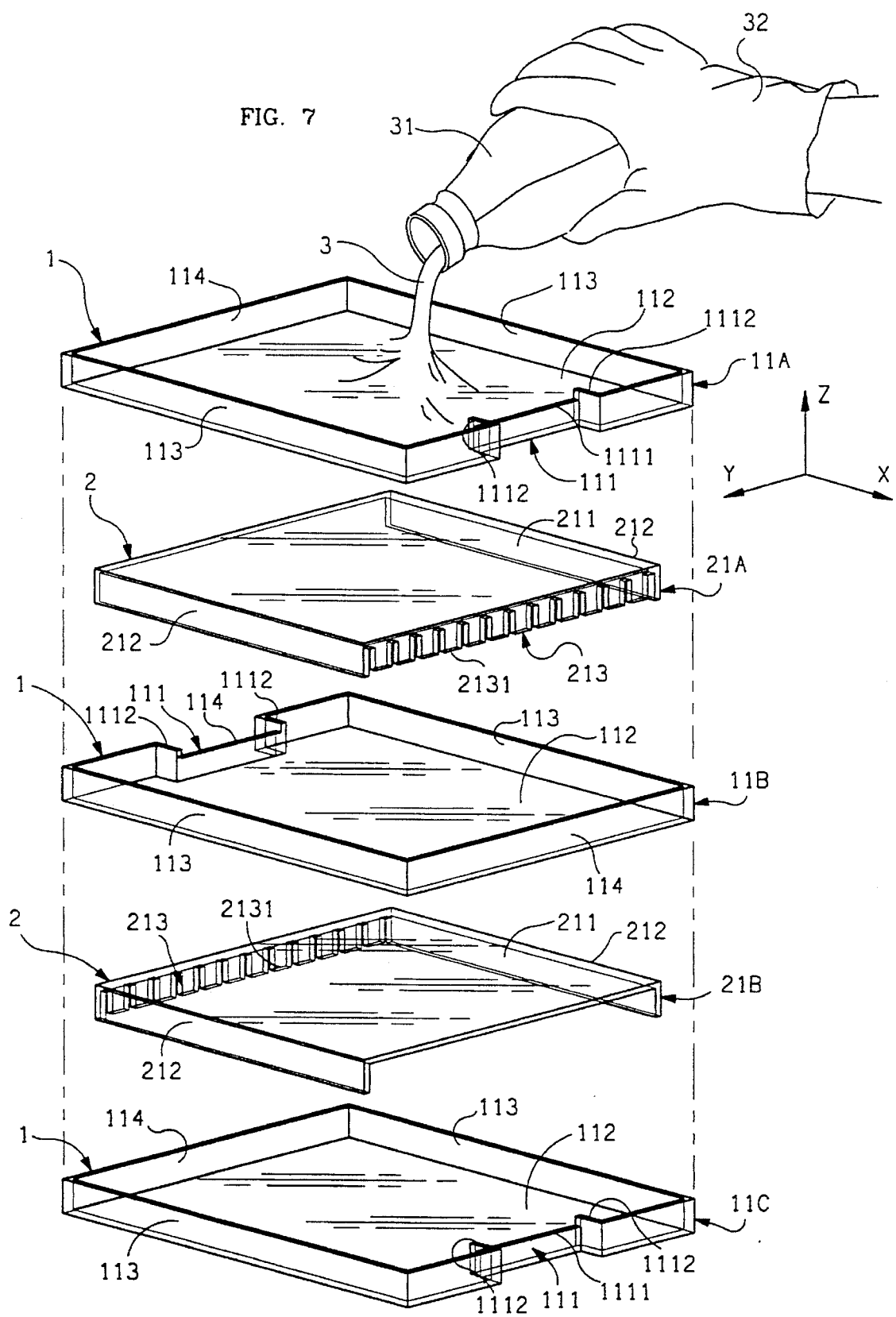
FIG. 7 is an exploded diagrammatic perspective view of a first preferred embodiment of vertically stacked trays, and also of a first embodiment of optional combination spacer-combs located between the trays, in accordance with the present invention, the trays and spacer combs being shown in operational use, in a manner most closely analogous to the prior art step previously shown in FIG. 3, to receive liquid that cascades downwards from tray to tray before congealing into electrophoresis gel.

Three replications of a first embodiment 11 of vertically stacked trays 1 in accordance with the present invention are shown in exploded diagrammatic perspective view in FIG. 7. Each tray 11A, 11B, 11C is possessed of a distinctive overflow feature 111, by which feature 111 alternate ones of the collective trays 11 may clearly be observed in FIG. 7 to be end-to-end reversed in the stack. Each tray 11A, 11B, 11C is, however, of like top-to-bottom orientation, presenting an upwardly disposed walled reservoir 112.

The combination spacers and combs, or spacer-combs 2, shown in FIG. 7 are optional, and will be discussed shortly. It may initially be envisioned in considering FIG. 7, and it may be considered as a first aspect of the present invention, that such spacer-combs 2 do not exist, and that the first embodiments 11 of the trays 1 simply rest directly on top of one another in an aligned vertical stack.

When the first embodiments of the trays 11 are so assembled in a vertical stack, or column, then a liquid 3, typically a heated slurry containing dissolved grains of agarose gel, is poured in the open reservoir 112 of the topmost tray 11A. It will be understood that neither the liquid 3, nor any container or bottle 31 from which the liquid 3 is poured, nor a human hand 32, is part of the present invention, and that these features are appropriately illustrated in phantom line in FIG. 7.

In accordance with the present invention, the poured liquid 3 accumulates in the reservoir 112 of the topmost tray 11A until the height of the lowest overflow point, or the overflow lip 1111 of the overflow feature 111, of this tray 11A is reached. At this time, the liquid 3 having assumed throughout the reservoir 12 a substantially even depth equal to the height of overflow lip 111, the liquid 3 will overflow the overflow lip 111 and pour downwards in the open top of the reservoir 112 of the next to topmost tray 11B. The reservoir 112 of this next to topmost tray 11B will ultimately become filled, and the liquid 3 will likewise pour from its respective overflow lip 111 into a next lowermost tray 11C. The process continues for so long as the liquid 3 is poured, and to such extent as the stack of trays 11 is high, the liquid 3 cascading downwards from tray to tray while filling the reservoir 112 of each tray 11A, 11B, 11C, etc. to a uniform even depth.

The alternating orientation of the overflow feature 111 of the trays 11 in the assembled stack clearly makes that the liquid 3 that overflows each tray (e.g. trays 11A, 11B) will fall downward only so far as the immediate next lowermost tray (e.g., into trays 11B, 11C), and will be completely caught and contained into the reservoir 112 of those trays. To promote a clean and dripless pouring between successive ones of the trays 11, it may be noted that the overflow feature 111 is possessed of sides 1112 that are of a height that is at least higher than the overflow lip 1111, and that are normally as high as is the remainder of the major sides 113 to each tray 11, and to its reservoir 112. These sides 1112 to the overflow feature 111 essentially cause all the liquid overflow to fall over the overflow lip 1111, only, and to flow cleanly into the reservoir 112 of an immediate next lower one of the trays 11 in the manner of a miniature waterfall.

Considering now the first embodiment 21 of the optional spacer-combs 2 shown in FIG. 7, these spacer combs 21 are interleaved between successive vertically stacked ones of the trays 11. The spacer-combs 21 are themselves in the general shape of a parallelepiped body of roughly the same size and aspect as the trays 11, and are commonly oriented so that a major, flat, surface 211 is disposed upwards. This flat surface 211 is integrally connects to two oppositely disposed sides 212, and to a comb 2131, that each extends perpendicularly downwards.

The first embodiment 21 of the spacer-combs 2 are preferably very slightly wider in the direction of the Y axis than are the trays 1. The slight additional width of the spacer-combs 21 over the trays 11 makes that the sides 212 of the spacer-combs 21 will fit to the exterior of the trays 11 in a manner that is most clearly seen in the detail view of FIG. 11. This construction simply prevents that an impression, or void, should be formed within the liquid 3, and ultimately within the gel formed from such liquid 3, within and at the sides of the interior reservoir 112 of each of the trays 11. In is undesirable that such a void, although small, should detract from the usable area of the gel that forms within the reservoirs 112 of the trays 11.

The spacer-combs 21 are must be, and are, substantially shorter in the direction of the X axis than are the trays 11. Each of the spacer-combs 21 is shorter than each of the trays 11 in the X axis direction by at least (i) the size of the overflow feature 111, and particularly the overflow feature sides 1112, in the X-axis direction, plus (ii) a small distance, nominally at least four (4) millimeters, by which the arrayed teeth 2131 of the comb 213 are desirably set apart from an end wall 114 of the reservoir 112 of a tray 11 that is immediately below the spacer-comb 21. The spacer-combs 21 are positioned roughly centrally in the X axis direction relative to the reservoir 112 of the underlying tray 11, and, because all the trays are aligned in a vertical stack, roughly centrally in the X axis direction relative to all of the vertically stacked trays 11. By this positioning, and by the relatively shorter length in the X direction of the spacer-combs 21 than the trays 11, an unobstructed straight line path in free space is realized from the overflow feature 111 of each tray 11 into the reservoir 112 of the next lowermost tray 11. In other words, the foreshortened spacer-comb 21, and most particularly its upper surface 211, neither extends nor is positioned so far in the X axis direction so as to interfere with the cascade of liquid 3 from tray to tray.

Meanwhile, the comb 213 of the spacer-comb 21 is simultaneously positioned so as to be spaced apart by a small distance, nominally four (4) millimeters, from the end side 114 of the reservoir 112 of the underlying tray 11. When so spaced the teeth 2131 of the comb 213 leave slits, or wells (not shown) in the gel state material that ultimately congeals from the liquid 3 at positions that are aligned with, and spaced apart from, the end side 114 of the reservoir 112 of the trays 11.

The relative alignment between the trays 11 and the optional spacer-combs 21 can be promoted by detentes, guide markings and other means known in the mechanical arts for the aligning mechanical assemblies of the nature of simple rectilinear blocks, Such secondary and subsidiary features are not shown in FIG. 7.

As in the prior art, the trays 1 are preferably fabricated from U-V transparent acrylic plastic to permit the direct reading of ethidium bromide stains. The acrylic plastic is normally at least 1/32" thick to prevent heat distortion of tray during application of hot agarose solution. Grooves may be placed in the trays 1, as will more particularly be shown in FIG. 15, to guide the placement of spacer-combs 2.

Meanwhile, the spacer-combs 2 may also be fabricated from typically transparent acrylic plastic, normally of 1/8" thickness. The spacer-combs 2 may also be fabricated from polycarbonate, Delrin™ plastic or Teflon™ plastic (Delrin™ and Teflon™ are trademarks of E. I. DuPont de Nemours and Company) by precision machining. It will be understood that the spacer combs 2 may have alternative numbers of teeth than that number illustrated in FIG. 7. The spacer combs 2 are typically fabricated with 1, 3 (one large well with two marker lanes on each side), 5, 10, 12, 16 or 20 wells in widths of 1.0 mm, 2.0 mm or 3.0 mm. Wider spacer-combs 2 used with 20 cm wide versions of the trays 1 typically come with 1.3 (one large well with two marker lanes on each side), 5, 8, 12, 16, 20, 30 or 40 wells at thicknesses of 1.0 mm, 2.0 mm or 3.0 mm.

Figure 8:
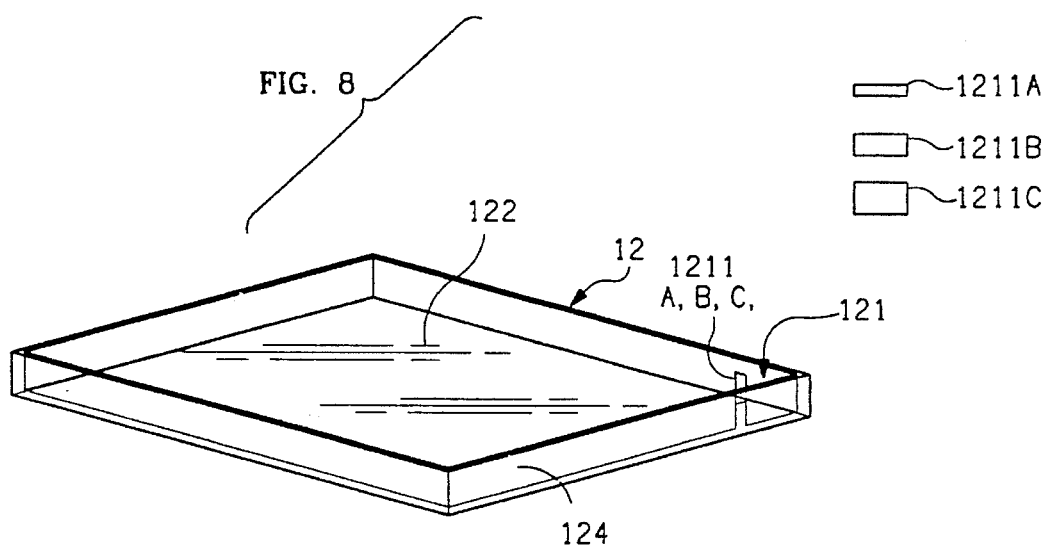
FIG. 8 is a diagrammatic perspective view of a second preferred embodiment of a vertically stacked tray in accordance with the present invention, the second embodiment tray being distinguished from the first embodiment tray previously shown in FIG. 2 for incorporating an overflow port at a one corner instead of along a short side of the tray.

A diagrammatic perspective view of a second preferred embodiment 12 of a vertically stacked tray 1 in accordance with the present invention is shown in FIG. 8. The second embodiment of the tray of the present invention, tray 12, is distinguished from the first embodiment of the tray of the invention, tray 11 previously shown in FIG. 7, for incorporating an overflow feature, or overflow port, 121 located at a one corner instead of midways along a short side 124 of the tray 12. The overflow feature, or port, 121 has and presents a small wall, or baffle, 1211. As with the height of the overflow lip 1111 of the overflow feature 111 of the tray 11 shown in FIG. 7, it is the height of this baffle 1211 that determines the depth, or thickness, to which liquid 3 (not shown in FIG. 8) will accumulate in the tray 12 before overflowing the tray 12 through its overflow port 121. The overflow lip 1211 is clearly not so high as the sides of the tray 12. (Just as the overflow lip 1111 of the overflow feature 111 of the tray 11 shown in FIG. 7 was not so high as the walls 113.)

Notably, however, it is intended that the baffle 1211—which is but a minute piece of inexpensive plastic—should be replaceable. Baffles 1211A, 1211B, 1211C of various heights may be placed in corresponding grooves (not shown) to the interior of the reservoir 122 of the tray 12 in order to predetermine the height to which the liquid 3 (not shown in FIG. 8, shown in FIG. 7) will rise before overflowing the tray 12, and to therefore predetermine the thickness of any gel that congeals in the tray 12.

Figure 9:
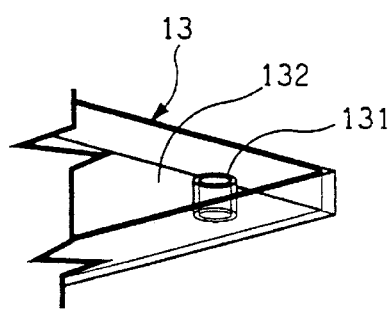
FIG. 9 is a partial, detail, diagrammatic perspective view of a third preferred embodiment of a vertically stacked tray in accordance with the present invention, the third embodiment tray being distinguished for incorporating a standpipe overflow port at a position spaced apart from the sides of the tray.

In a similar vein, a partial, detail, diagrammatic perspective view of a third preferred embodiment 13 of a vertically stacked tray 1 in accordance with the present invention is shown in FIG. 9. The partial view is of the overflow feature, now in the form of a small standpipe 131. The standpipe 131, which serves as the overflow port, is preferably positioned as shown slightly spaced apart from the sides of the tray 13. This is so that the liquid 3 (not shown in FIG. 9, shown in FIG. 7 overflowing through the standpipe 131 will flow in to the reservoir 132 of a next lowermost one of a vertically stacked and aligned column of trays 13 without dripping over the edges of such next lowermost tray 13. The standpipe 131 may be threaded at its base (not shown), and received into a complimentary screw cavity within the body of tray 13. The threaded standpipe 131 may be screwed under force of the fingers to various depths of insertion within the tray 13, thus to variably predetermine the height to which the liquid 3 (not shown in FIG. 9, shown in FIG. 7) will rise before overflowing the tray 13, and to therefore predetermine the thickness of any gel that congeals in the tray 13. Notably, it should be considered that lower, or evacuation, end of the standpipe 131 may extend beyond the body of tray 13, and into free space, without interference with any stacking of successive trays 13, or with the cascaded overflow operation of the present invention.

All embodiments of the trays 1 of the present invention as trays 11–13 shown in FIGS. 7–9 are intended to be (i) stacked, and (ii) end-to-end reversed in the stack from one to the next in order that a best even flow distribution of the fluid 3 may be obtained in each upper one of such trays 1 before cascading to a next lower one of such trays 1.

In accordance with the three embodiments of the trays 1 already described (embodiments 11, 12 and 13 respectively shown in FIGS. 7, 8 and 9), it will be recognized by a practitioner of the mechanical design arts that the construction of vertically stacked array of successive overflowing reservoirs in the manner of an ancient water clock could be realized in many different ways. In this regard, and as an example, and optional feature of any of the embodiments 11, 12, 13 of a tray 1 of the present invention is shown in partial, detail, diagrammatic perspective view in FIG. 10. A detente 14, preferably located as illustrated at the corner, and more preferably at each of the four corners, of any of the embodiments 11, 12, or 13 of the trays 1 helps to locate and to maintain the stacked trays 1 in uniform precise alignment one to the next.

The present invention is further possessed of different, and alternative, elements than the stacked trays 1 and the gel production system based thereon. Particularly, the comb portion 213 of the combination spacer and comb, or spaced comb, or spacer-comb 21 is an invention in of itself; which invention is completely separate and severable from the stacked trays 1 and the system based thereon. Namely, the comb 213 of the spacer-comb 21 is itself, and without more, usable to rest in a tray, any tray, (i) during the pouring of a liquid into a reservoir of the tray, and, subsequent to the partial filling of the reservoir with the liquid, (ii) the gelling of the poured liquid into a gelatin state material. The comb 213 is subsequently extracted from the gelatin state material, leaving a array of slits, or wells.

Figure 11:
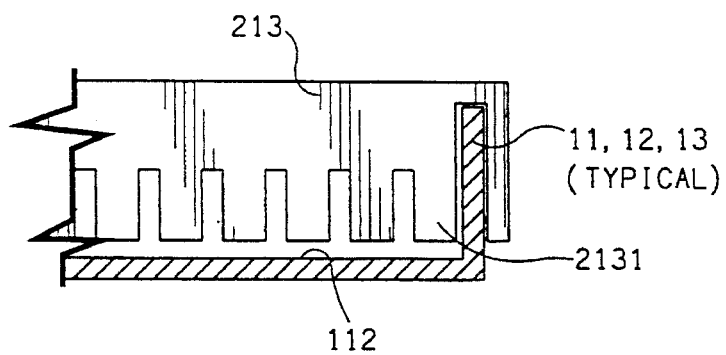
FIG. 11 is a cut-away detail view of a comb, such as may be a part of the preferred embodiment of the optional combination spacer-comb that was previously seen in FIG. 7, positioned in relation to a tray in accordance with the present invention, which tray was previously seen in FIGS. 7–9.

A partial, detail, diagrammatic perspective view of a preferred embodiment of a comb 213 in accordance with the present invention is shown in FIG. 11. The spacer-comb may be, and preferably is, part of the selfsame spacer-comb 21 that is shown in FIG. 7. However, it should clearly be understood and envisioned that the comb 213 may be simply a toothed bar, or strip, in the substantial two-dimensional flat aspect of a common hair comb, and that the comb need not be associated with any further, nor more extensive, spatial body (such as, for example, the parallelpiped body of spacer-comb 21 shown in FIG. 7).

Figure 10:
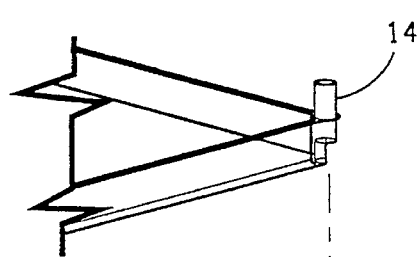
FIG. 10 is partial, detail, diagrammatic perspective view of an optional detente feature that may be incorporated into any of the embodiments of vertically stacked trays in accordance with the present invention.

Referencing FIG. 10, the comb 213 satisfies two criteria. It spans between opposing walls (of which one such wall is shown) of the reservoir 12 of a tray 11, 12, or 13 (typical); and when so positioned its teeth 2131 extend downwards into the reservoir 12 to a depth that is commonly above the bottom of the reservoir. When it is so positioned the teeth 2131 of the comb 213 will produce a linear array of spaces, or voids, in any liquid 3 (not shown in FIG. 10, shown in FIG. 7) that is entered into the tray 11, 12, 13 (typical), and corresponding array of spaces, or voids, or slits, or wells in any gel state material that is congealed from the liquid.

The clear advantage of the comb 213, alone and without more, in the process of producing one or more trays of gel state material from congealed liquid is that the comb 213 may be inserted into the tray at a location where wells are ultimately desire prior to pouring the liquid into the tray, and, subsequently to letting gel a liquid poured into the tray, the comb 213 may be conveniently, quickly and easily extracted so as to leave a predetermined array of perfectly positioned wells of a predetermined perfect uniform depth.

A diagrammatic perspective view of a second preferred embodiment 22 of an optional combination spacer-comb 2 that is located between the trays 1 (previously seen in FIGS. 7–9) is shown in FIG. 12. The embodiment 22 is characterized by having a top surface that is not coextensive with the width of a tray 1.

A diagrammatic perspective view of a third preferred embodiment 23 of an optional combination spacer-comb 2 that is located between the trays 1 (previously seen in FIGS. 7–9) is shown in FIG. 13. The embodiment 23 is characterized by having two separate portions 231 and 232. Typically only one portion (portion 232) mounts a comb.

A diagrammatic perspective view of a fourth preferred embodiment 24 of an optional combination spacer-comb 2 that is located between the trays 1 (previously seen in FIG. 7) is shown in FIG. 14. The embodiment 24 is characterized by being adjustable in the distension of its two separate portions 241 and 242 by action of screw 243. Only the one portion 242 mounts the comb. Because this comb portion 242 is adjustable relative to portion 241 that engages the sides of a tray 1 (shown in FIG. 7), the height above the base of such tray of the slits, or wells, created by the comb portion 242 is infinitely adjustable over a range of typically 0 to 4 mm.

A partial, detail, diagrammatic perspective view of the interaction of any of the embodiments of spacer-combs 21–24 previously seen in FIGS. 7 and 12–14 with an optional detente feature 131 that may be incorporated into any of the embodiments of vertically stacked trays 1 in accordance with the present invention is shown in FIG. 15. The function of the detente, and like detentes not shown, to precisely locate a spacer-combs 21–24 is routine. Note that the feature of the spacer-combs 21–24 that engages the detent may be internal or external to the reservoir of the trays 1.

A partial detail view of several embodiments of an adjustable fifth preferred embodiment 25 of an optional combination spacer-comb 2 that is located between the trays 1 (previously seen in FIG. 7) is shown in FIG. 16, consisting of FIGS. 16a through 16e. Each combination spacer-comb 25 engages complimentary features on a complimentary embodiment of a tray 1 so as to locate the spacer-comb 25 relative to the tray, and to the gel 3 (shown in FIG. 7) therein.

In accordance with the preceding explanation, variations and adaptations of the each of (i) the vertically stacked trays overflowing liquid congealing into electrophoresis gel, (ii) the optional combination spacer-combs between the trays, and (iii) the combs (alone) in accordance with the present invention will suggest themselves to a practitioner of the mechanical arts.

For example, the trays need not be of uniform size nor depth of fill but could, in accordance with the individual gels desired to be made with the individual trays, could comprise a set of related, and functionally operative, trays. For example, the overflow feature(s) could be physically separated from the trays, and instead incorporated into a multi-tier free-standing fluid distribution column, much in the manner of a water clock, that would interlock and flow connect a corresponding tier of trays. The trays themselves would then be featureless parallepiped bodies each one of which, when arrayed in the stack or tier, simply flow-communicated with a corresponding level of the fluid distribution column. In this construction the fluid distribution column would incorporate the overflow features, and the resulting downwards cascade of fluid. As the fluid was successively distributed to each level in the fluid distribution column it would flow from that column level into the associated tray. Only when the fluid in all trays had gelled would any, and all, trays be separated from the column, For example, if the comb function of the spacer-combs is foregone, mechanical elements of innumerable configurations will serve as simple spacers (to such extent as such spacers are even necessary or desired, generally being optional) between the trays. For that matter, even an element performing both the functions of (i) spacer and (ii) comb in combination may be substantially physically dissimilar from that particular embodiment of a spacer-comb 2 illustrated in FIG. 7. It might be envisioned, for example, that the entire spacer-comb element was in the sparse shape of three walls forming a "U", or even two walls forming an "L". The illustrated preferred embodiments of the invention will be understood to be a compromise between undue elaboration, which is not desired, and such an ultra minimalist structure as, while performing the diverse functions of the present invention, would appear insubstantial and unsound to a human who is, after all, typically investing some dollars of cost in material and labor into the preparation of agarose gels.

Finally, and for example, one the concept of an in-situ comb in accordance with the present invention is understood, there are many ways of realizing such a function. A comb might be an integrally molded part of a disposable tray. The comb would be frangible, and detachable for the tray. After a gel was formed in the tray, replete with a desired wells as were created by the teeth of the comb, the comb could be broken off, and discarded.

In accordance with these and other possible variations and adaptations of the present invention, the scope of the invention should be determined in accordance with the following claims, only, and not solely in accordance with those particular embodiments within which the invention has been taught.

What is claimed is:

1. A method of preparing flat sheets of a gel state material suitable to receive samples upon which electrophoresis may be performed, the method comprising:

vertically stacking in a vertical stack
- a plurality of trays each having (i) a base and sides defining a substantially flat substantially shallow interior reservoir, (ii) an overflow outlet from which liquid received into the reservoir will flow out of the reservoir when a predetermined liquid level is reached in the reservoir, and (iii) a top opening located so that it may be disposed in position below the overflow outlet of any immediately overlying tray in the vertical stack of trays, interleaved with
- a plurality of spacers inserted between successive ones of the vertically stacked plurality of trays, each a spacer at least partially in the aspect of a comb having downwards extending teeth;
- wherein, by the interleaved stacking of trays and of spacers having at least the partial aspect of a comb having downwards extending teeth, an array of small volumes in the reservoir of each tray that supports a spacer is protected by the teeth features of the spacer against any incursion of liquid;

pouring a liquid material that will gel to a gel state into an uppermost one of vertically stacked trays so that the liquid fills the reservoir of this uppermost tray to a predetermined height it will then overflow through the overflow outlet of this uppermost tray, flowing downwards into the reservoir of a next lower tray and successively cascading downwards from tray to tray as the reservoir of each tray is filled to a uniform even level until, ultimately, a reservoir of bottom one of the stacked trays is reached and filled with the liquid material;

letting the liquid material in each tray gel so as to form a gel state material suitable to receive samples upon which electrophoresis is conducted; and removing the at least one spacer upon the gelling of the liquid material, leaving an array of voids in the gel state material suitable to receive the samples upon which electrophoresis is ultimately conducted;

wherein a plurality of trays each containing flat sheets of a gel state material suitable to receive samples upon which electrophoresis may be performed have been simultaneously prepared.

2. The method according to claim 1 wherein at least one of the plurality of spacers that are inserted between successive ones of the vertically stacked plurality of trays is thicker in the vertical stack than is a lower tray in the stack into the reservoir of which lower tray the teeth features of the at least one spacer extend;

wherein the liquid material drips in air from at least one of the plurality of trays to a next lower one of the plurality of trays.

3. A covered tray suitably used with a number of identical covered trays in order to prepare in each tray from a liquid material poured into a reservoir of the covered tray a flat sheet of a gel state material suitable to receive samples upon which electrophoresis may be performed, each covered tray comprising:

a tray body suitably vertically stacked with a number of other tray bodies in a vertical stack, the tray body having and defining a substantially flat interior reservoir, an overflow outlet from which liquid received into the reservoir will flow out of the reservoir when a predetermined liquid level is reached in the reservoir, and a top opening located so that it may be disposed in position below the overflow outlet of any immediately overlying tray body in the vertical stack of tray bodies;

a cover member at least partially overlying the reservoir of each tray body and to the extent so overlying the reservoir forming a cover thereto, the cover member having and presenting teeth in the manner of a comb which teeth extend, when the cover member is overlying the reservoir, into the reservoir, therein to establish within the reservoir an array of small volumes into which volumes any liquid poured into the reservoir cannot enter;

wherein, when a liquid material is poured into the tray body while the cover member is in place at least partially overlying the tray body's reservoir, and after the liquid material is allowed to gel to a gel state, a separation of the cover member from the tray body leaves an array of voids in the gel state material that is within the tray body's reservoir, the voids being suitable to receive samples upon which electrophoresis transpires.

4. The covered tray according to claim 3 wherein the interior reservoir to the tray body is substantially rectangular in area; and wherein the overflow outlet to the reservoir is located at at least one corner of the rectangular area.

5. The covered tray according to claim 3 wherein the reservoir of the tray body is more specifically defined by an upper surface to a bottom of the tray body, and by interior surfaces to sides of the tray body;

wherein the overflow outlet is spaced above the upper surface of the bottom of the tray body so that any poured liquid entering the tray body through its opening will accumulate in the tray body to the predetermined level before exiting the reservoir through the overflow outlet; and wherein the overflow outlet is spaced apart from the interior surfaces of the walls so that, should a liquid exit the tray body through the overflow outlet and pour through a top opening into a reservoir of an underlying identical tray body vertically aligned in the vertical stack of tray bodies, then the liquid will so enter into the reservoir of this underlying tray body cleanly while contacting naught but the upper surface of the bottom, and by the interior surfaces of the sides, of this underlying tray body;

wherein any liquid flowing though the overflow outlets of successive ones of vertically stacked tray bodies passes cleanly from the reservoir of each higher tray body to the reservoir of a next lower tray body without coming into contact with any surface of any tray bodies save only the upper surface of the bottom, and the interior surfaces of the sides, of each tray body's reservoir.

6. The covered tray according to claim 3 wherein the reservoir of the tray body is more specifically defined by an upper surface to a bottom of the tray body, and by interior surfaces to sides of the tray body;

wherein the overflow outlet is in the form of a standpipe with a top opening spaced above the upper surface of the bottom of the tray body;

wherein any poured liquid entering the tray body through its opening will accumulate in the tray body to the predetermined level equal to the height of the standpipe above the upper surface to a bottom to the tray body before exiting the reservoir.

7. An apparatus for preparing from a liquid material a flat sheet of a gel state material having land defining an array of wells each of which is suitable to receive a sample upon which electrophoresis may be performed, the apparatus comprising:

a tray having a base and sides defining a substantially flat interior reservoir, the tray suitably vertically stacked with a number of other trays in a vertical stack, the tray body having and defining an overflow outlet from which liquid received into the interior reservoir will flow out of the reservoir when a predetermined liquid level is reached in the reservoir, and also a top opening located so that it may be disposed in position below the overflow outlet of any immediately overlying tray in the vertical stack of trays; and a member at least partially overlying the reservoir of the tray and to the extent so overlying the reservoir forming a cover thereto, the member having and presenting teeth in the manner of a comb which teeth extend, when the member is overlying the reservoir, into the reservoir, therein to establish within the reservoir an array of small volumes into which volumes any liquid poured into the reservoir cannot enter;

wherein, when a liquid material is poured into the tray while the member is in place at least partially overlying the tray's reservoir, and after the liquid material is allowed to gel to a gel state, a separation of the member from the tray leaves an array of voids in the gel state material that is within the tray's reservoir, the voids being suitable to receive samples upon which electrophoresis transpires.

* * * * *